United States Patent [19]

Hoe

[11] Patent Number: 4,767,331

[45] Date of Patent: Aug. 30, 1988

[54] DENTAL CROWN MANUFACTURING APPARATUS

[76] Inventor: Khin A. Hoe, 1501 SE. 23rd Ave., Pompano Beach, Fla. 33062

[21] Appl. No.: 55,018

[22] Filed: May 28, 1987

[51] Int. Cl.$^4$ ............................................. A61C 11/00
[52] U.S. Cl. ........................................ 433/213; 433/60
[58] Field of Search ............................ 433/213, 34, 60

[56] References Cited

U.S. PATENT DOCUMENTS

| | | | |
|---|---|---|---|
| 1,822,043 | 9/1931 | Kohler | 32/71 |
| 3,937,773 | 2/1976 | Huffman | 264/17 |
| 4,398,884 | 8/1983 | Huffman | 433/74 |

Primary Examiner—Carroll B. Dority, Jr.
Attorney, Agent, or Firm—Oltman and Flynn

[57] ABSTRACT

A tooth positioning kit in a dental model enabling the lateral and outward adjustment of a neighbor tooth on either side of a tooth being fitted with a crown. The kit comprises a receptacle fixedly positioned in the base of the dental model, interchangeable first and second adapters for insertion in and removal from the receptacle, and a tooth-support insert that is attached to the neighbor tooth and the corresponding gum segment and is insertable in and removable from either adapter. When the first adapter is in the receptacle and receives the tooth-support insert, the neighbor tooth is at the exact position of the corresponding tooth in the patient's mouth. When the second adapter is in the receptacle and receives the tooth-support insert, the neighbor tooth is farther away from the tooth being fitted with a crown and is farther out from the base of the dental mold.

17 Claims, 3 Drawing Sheets

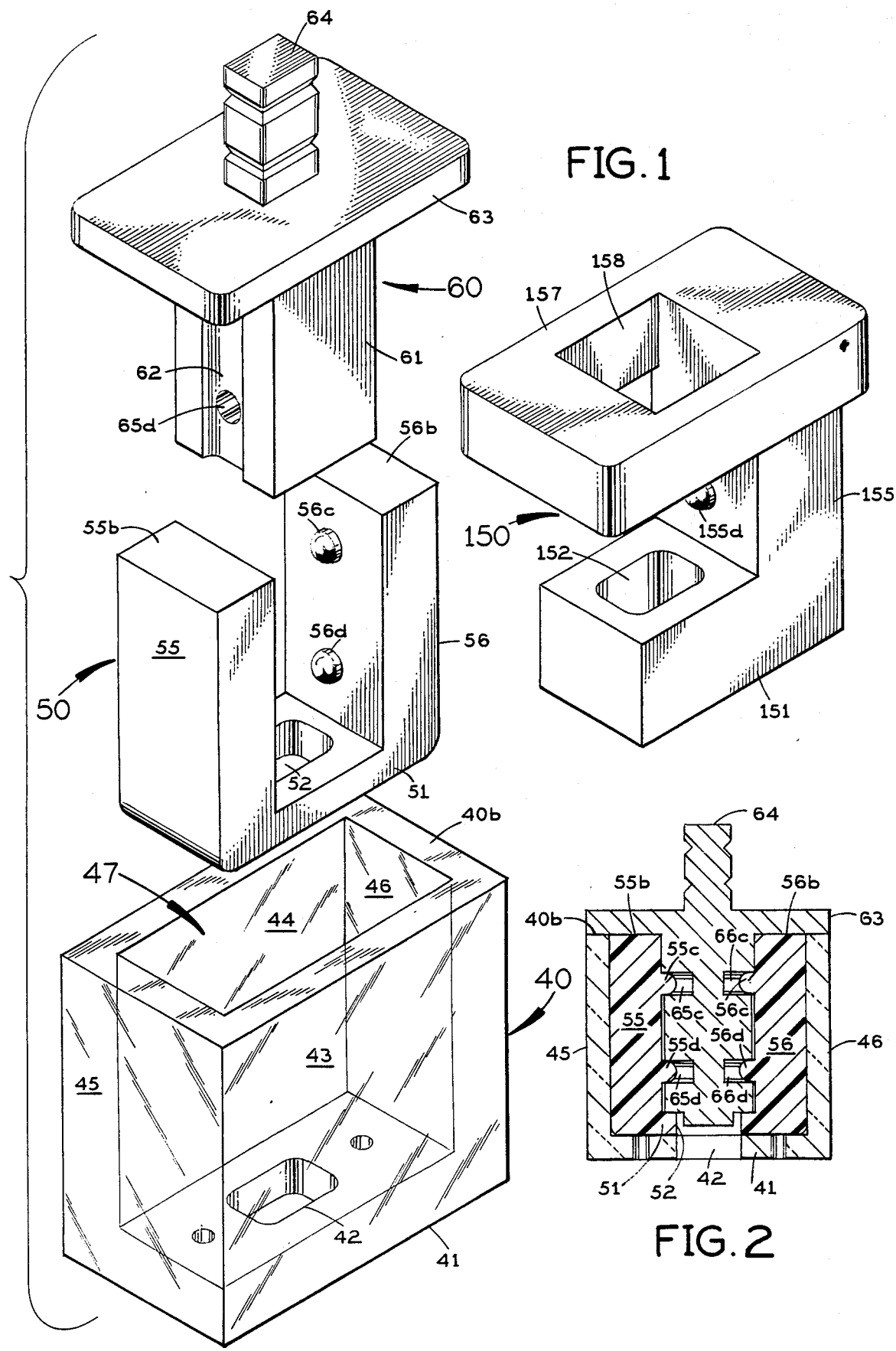

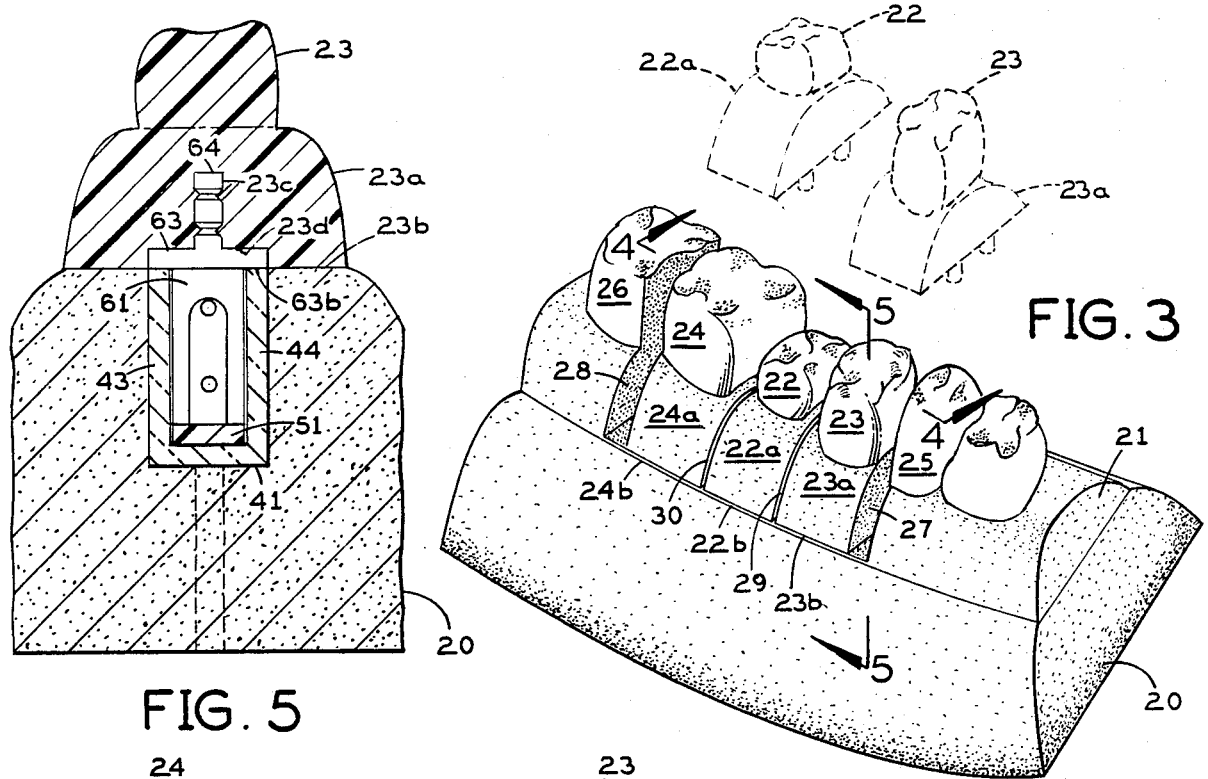

DENTAL CROWN MANUFACTURING APPARATUS

SUMMARY OF THE INVENTION

This invention relates to the manufacture of dental crowns.

One principal object of this invention is to provide an apparatus enabling the manufacture of a dental crown more conveniently and more quickly, and therefore at lower cost.

Another principal object of this invention is to provide a novel kit for use in a dental model in the manufacture of a dental crown.

The standard practice in manufacturing a dental crown is to use a dental model which is a duplicate of the patient's teeth and gum at and near the tooth to be crowned. The duplicate of the tooth to be crowned and the corresponding gum segment are removable as a unit from the rest of the model. For convenience, this tooth-and-gum unit in the dental model is referred to hereinafter as the "crown tooth unit", and the tooth that is to be fitted with a crown is referred to as the "crown tooth". A thin metal coping is adhesively attached to this crown tooth and then a wet mixture of porcelain powder and distilled water is applied to this coping. The crown tooth unit is removed from the model and baked in an oven, where the porcelain-water mixture undergoes shrinkage of about 1.0 mm. on the top and 0.5 mm. on each side. Then crown tooth unit is reinserted into the model and the dental technician determines whether the baked porcelain crown has precisely the correct size and shape. Additional porcelain may have to be added to the crown to build it up to the correct size.

A certain amount of estimation or guess work is involved because of the shrinkage in the oven each time the crown is baked. The size of the crown in the model when the porcelain is wet is larger than it will be after baking. This creates a problem in removing the crown tooth unit with the slightly oversized wet porcelain crown from the model for baking.

The present invention solves this problem by making the neighbor teeth in the plaster model on each side of the crown tooth laterally adjustable toward and away from that tooth. Each of these neighbor teeth has one lateral position which is precisely the same as the position of the corresponding tooth in the patient's mouth. Each neighbor tooth has one or more additional positions in which it is farther away from the crown tooth. This makes it easier for the dental technician to apply wet porcelain to build up the crown, also to remove the crown tooth unit with the wet porcelain crown from the model for baking, and to reinsert the crown tooth unit with the baked porcelain crown back in the model.

In accordance with the presently-preferred embodiment of this invention, the lateral adjustability of each neighbor tooth in the plaster model is provided by interchangeable first and second adapters which fit in a receptacle anchored in the base of the model and each adapted to receive an insert on which that neighbor tooth and the corresponding gum segment are mounted. The first adapter is shaped and dimensioned so that, when in the corresponding receptacle, it positions the neighbor tooth in the model at the exact position of the corresponding tooth in the patient's mouth. When the second adapter is in that receptacle it positions that tooth in the model farther from the crown tooth than the corresponding tooth in the patient's mouth, thereby enabling the crown to be "packed" with wet porcelain and enabling the crown tooth unit to be removed from the dental model without interference with the neighbor tooth. Also, the second adapter positions the neighbor tooth farther out from the base of the dental model than the first adapter does, thereby compensating during the "packing" of wet porcelain on the crown for the later shrinkage of the porcelain when it is baked and minimizing the guess work involved in getting the baked crown even with the neighbor teeth in a direction outward from the gum.

Essentially the same technique is used in the manufacture of a multiple-tooth crown in accordance with the present invention.

Further objects and advantages of this invention will be apparent from the following detailed description of a presently preferred embodiment which is illustrated schematically in the accompanying drawings.

DESCRIPTION OF THE DRAWINGS

FIG. 1 is a perspective view of the tooth positioning kit in accordance with the present invention, including the alternate first and second adapters;

FIG. 2 is a longitudinal section through the assembled kit with the first adapter in place;

FIG. 3 is a perspective view showing a dental model which duplicates part of a dental patient's teeth and gum, with a tooth to be fitted with a crown (i.e., the "crown tooth") and neighboring teeth on both sides of it (and the corresponding gum segments) individually removable;

FIG. 4 is a vertical longitudinal section taken along the line 4—4 in FIG. 3;

FIG. 5 is a vertical cross-section taken along the line 5—5 through one of the neighbor teeth next to the crown tooth;

FIG. 6 is a perspective view of the crown tooth and the coping of the crown;

FIG. 7 is a perspective view of a spacer which may be used in the present kit;

Figure 8:
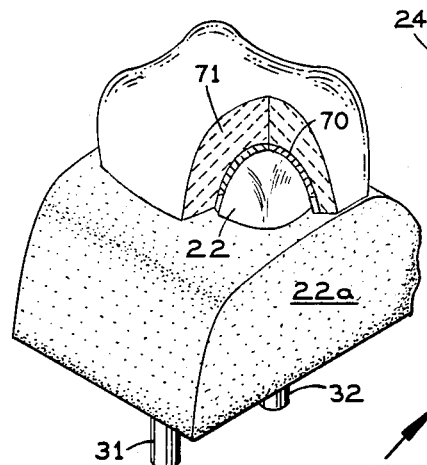
FIG. 8 is a perspective view, with parts broken away for clarity, of the crown tooth unit.
Figure 9:
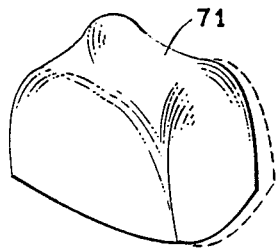
FIG. 9 is a perspective view of the crown, with added-on porcelain on one side shown in phantom.

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

DETAILED DESCRIPTION

Referring to FIG. 3, in the manufacture of dental crowns the usual practice is to make a plaster duplicate of the area in the patient's mouth which includes the tooth to be crowned. This plaster duplicate includes a base 20, a gum portion 21 on top of the base which duplicates the patient's gum, and several teeth on top of the gum portion which duplicate the patient's actual teeth. These include the artificial tooth 22 which is to be fitted with a crown (the "crown tooth"), a neighbor tooth 23 on one side of crown tooth 22, a neighbor tooth 24 on the opposite side of crown tooth 22, and teeth 25 and 26 on the opposite sides of the respective neighbor teeth 23 and 24 from the crown tooth 22 between them. The dentist prepares the patient's natural tooth that is to be crowned by removing enough tooth material to leave a space all the way around it. This space will be occupied by the crown.

In accordance with the present invention, next to the neighbor tooth 23 a cut about 1.0 millimeter wide is made through tooth 25 and the underlying part of the gum portion 21. This leaves a gap as shown at 27 in FIG. 3. A similar cut is made next to the other neighbor tooth 24 through tooth 26 and the underlying part of gum portion 21, leaving a gap as shown at 28. Narrower cuts 29 and 30 are made on opposite sides of tooth 22 through the gum portion 21 beneath it. Also, a narrow horizontal cut 22b is made from front to back along the bottom of gum portion 21 between cuts 29 and 30. This leaves a gum segment 22a joined to tooth 22 and separated from base 20 and the rest of gum portion 21. Narrow horizontal cuts 23b and 24b are made from front to back along the bottom of gum portion 21 between cuts 27 and 29 and between cuts 30 and 28. This leaves a gum segment 23a joined to neighbor tooth 23 and separated from the rest of gum portion 21 and the base 20, and a gum segment 24a joined to the other neighbor tooth 24 and separated from the rest of gum portion 21 and the base 20.

With this arrangement, the crown tooth 22 and the corresponding gum segment 22a are removable as a unit from the base 20. This unit 22-22a will be referred to as the "crown tooth unit". Neighbor tooth 23 and its gum segment 23a are similarly removable as a unit, and the other neighbor tooth 24 and its gum segment 24a are removable as a unit. Each unit 23-23a and unit 24-24a will be referred to as a "neighbor tooth unit". Each of these tooth-and-gum units is independently removable. For example, crown tooth unit 22-22a is removable as a unit while the neighbor teeth units 23-23a and 24-24a remain in place on the base 20.

The wide gaps 27 and 28 enable the respective neighbor teeth 23 and 24 to be positioned laterally away from the crown tooth 22, as explained hereinafter.

In accordance with the usual practice, the crown tooth unit 22-22a has a pair of locating pins 31 and 32 (FIG. 6) extending down below gum segment 22a, as shown in FIG. 6. Pin 32 is spaced behind pin 31 and is longer than it. These pins are snugly but slidably received in corresponding cylindrical sockets anchored in vertical recesses in the base 20, as shown for pin 31 in FIG. 4. The socket which receives this pin is designated by the reference numeral 33 in this Figure. When the pins 31 and 32 are in place in the corresponding sockets in base 20, they position the crown tooth unit 22-22a exactly as the patient's corresponding natural tooth and gum segment are in the patient's mouth.

In accordance with the present invention, each neighbor tooth segment 23-23a and 24-24a, is positioned on the base 20 by a positioning kit as shown in FIG. 1.

This kit includes a rectangular, open-topped receptacle 40 which is permanently anchored in base 20 so that the flat top surface 40b of this receptacle is flush with the top surface 20b (FIG. 4) of the base where the corresponding gum segment 23a or 24a was cut away. Receptacle 40 has a flat bottom wall 41 with a laterally elongated oblong opening 42, flat front and back walls 43 and 44 extending perpendicularly up from this bottom wall, and opposite end walls 45 and 46 extending perpendicularly up from the bottom wall between the front and back walls. The receptacle defines a recess 47 of rectangular cross-section that is relatively deep from the open top down to the bottom wall 41. In one practical embodiment each wall of the receptacle is about 0.5 millimeter thick. For a posterior tooth the outside dimension of the receptacle 40 from end to end is about 5 millimeters, and for an anterior tooth this dimension of the receptacle is about 3.5 millimeters.

The second part of the kit is a set of interchangeable adapters, each of which is slidably receivable in and removable from the recess 47 in receptacle 40. As shown in FIG. 1, one adapter is a generally channel-shaped or U-shaped integral member 50 which is in the receptacle 40 when the neighbor tooth 23 or 24 is to be positioned at the exact position of the corresponding tooth in the patient's mouth. When each neighbor tooth is to be positioned farther from the artificial tooth 22 that is being fitted with a crown, a second adapter 150 is received in the receptacle recess 47.

The channel-shaped or U-shaped first adapter 50 has a flat bottom wall 51 with an oblong opening 52 that registers with the bottom opening 42 of receptacle 40 when this adapter is received in the receptacle. The first adapter has opposite end walls 55 and 56 extending perpendicularly up from its bottom wall. The outside end-to-end dimension of adapter 50 is just slightly less than the end-to-end dimension of the receptacle recess 47 (e.g., 4 mm.) so that the first adapter fits snugly but slidably inside the receptacle 40 as shown in FIG. 2. The end walls 55 and 56 of adapter 50 have respective flat top surfaces 55b and 56b which are substantially even with the top face 40b of receptacle 40 when this adapter is seated in the receptacle. The end wall 56 of adapter 50 has a pair of vertically spaced, rounded projections 56c and 56d on the inside, as shown in FIGS. 1 and 2. The other end wall 55 of the adapter, as shown in FIG. 2, has a pair of similarly located rounded projections 55c and 55d on the inside. In one practical embodiment, the bottom wall 51 of adapter 50 is about 0.5 mm. thick and each of its end walls 55 and 56 is about 1 mm. thick when it is for use with a receptacle 40 having an end-to-end outside dimension of 5 mm. (i.e., for a posterior tooth).

Figure 10:
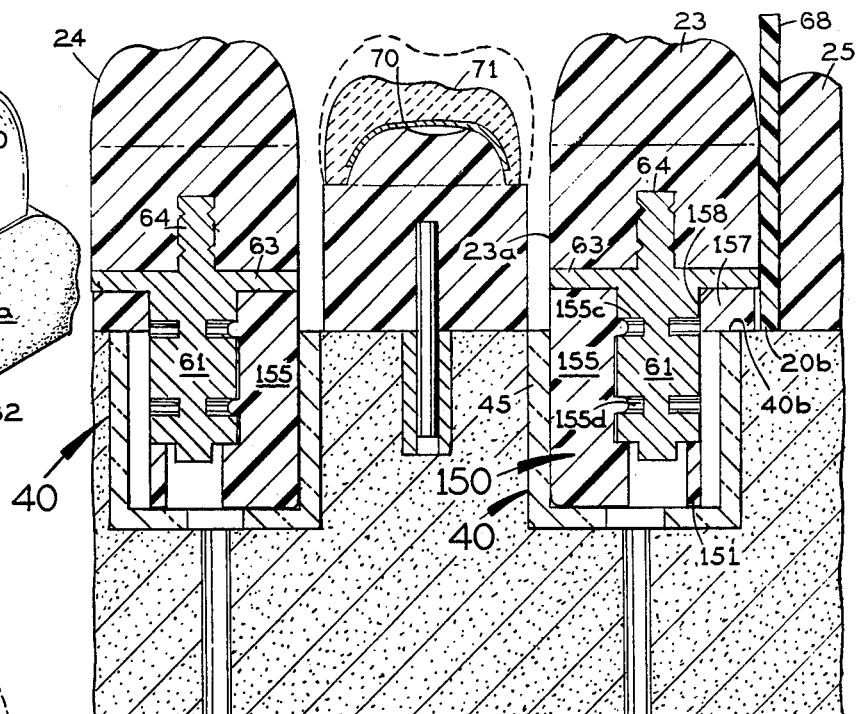
FIG. 10 is a vertical longitudinal section generally similar to FIG. 4 and showing the second adapter in place in the tooth positioning kit for a neighbor tooth next to the crown tooth and also showing the FIG. 8 spacer in its operative position.

When the first adapter 50 is received in receptacle 40, together they provide a first socket of rectangular cross-section. This socket is defined by the front and rear walls 43 and 44 of the receptacle and the bottom wall 51 and end walls 55 and 56 of the first adapter. As shown in FIG. 10, this first socket is open toward the gum segment 23a or 24a for the corresponding neighbor tooth 23 or 24.

The third part of the kit is an insert 60 that is removably held by the first adapter 50 or the second adapter 150. Insert 60 has a bottom segment 61 of generally rectangular cross-section that fits snugly in the first socket between the first adapter end walls 55 and 56 and between the receptacle front and rear walls 43 and 44. At its left end in FIG. 1, this bottom segment 61 of the insert is formed with a shallow groove 62 enabling it to be slid down over the rounded protrusions 55c and 55d on the inside of the adapter end wall 55, as well as a similar shallow groove in its right end face (not visible in FIG. 1) enabling it to be slid down over the rounded protrusions 56c and 56d on the inside of the adapter end wall 56. At these grooves the insert segment 61 presents recesses or depressions 65c and 65d (FIGS. 1 and 2) and 66c and 66d (FIG. 2) which snugly received the corresponding rounded protrusions 55c, 55d, 56c and 56d on the adapter end walls.

Joined to the bottom segment 61 of the insert 60 is a generally rectangular, flat, top segment 63 which projects beyond the bottom segment on all sides. As shown in FIG. 2, this top segment is in overlying engagement with the top surfaces 55b and 56b of the adapter end walls 55 and 56 and with the top surface 40b of receptacle 40 when these parts of the kit are assembled together.

Insert 60 has a laterally grooved post 64 of generally rectangular cross-section extending up from its top segment 63 and adapted to be snugly received in a complementary recess 23c in the gum segment 23a for the corresponding neighbor tooth 23, as shown in FIGS. 4 and 5, so that this tooth, the corresponding gum segment 23a and insert 60 can be handled as a unit. As shown in FIG. 5, the gum segment 23a is formed with a bottom recess 23d which snugly receives the top segment 63 of insert 60 so that the bottom face 63b of segment 63 is even with the cut 23b separating gum segment 23a from base 20.

Figure 11:
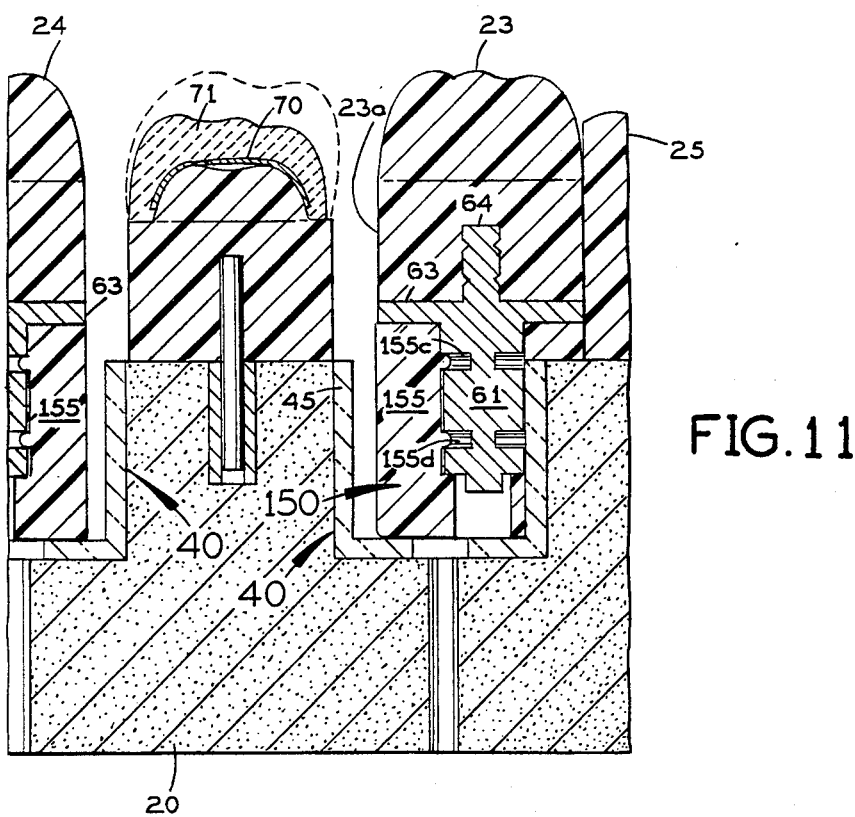
FIG. 11 is a view similar to FIG. 10 with the spacer removed and the neighbor tooth retracted even farther from the crown tooth.

The second adapter 150 (FIG. 1) in the positioning kit has a flat bottom wall 151 that is 1 mm. thicker than the bottom wall 51 of the first adapter 50 and has an oblong opening 152 for registration with the bottom opening 42 in receptacle 40. The second adapter has a single end wall 155 extending up from its bottom wall 151 at one end and having the same height as, and a greater thickness than, either end wall 55 or 56 of the first adapter 50 but less than their combined thicknesses. Where the receptacle recess 47 has an end-to-end dimension of 4 mm., end wall 155 is 1.5 mm. thick (in the end-to-end direction) and bottom wall 151 extends 2 mm beyond end wall 155 in that same end-to-end direction. A pair of vertically spaced rounded protrusions 155c and 155d (FIGS. 10 and 11) on the inside of end wall 151 are receivable snugly in recesses 65c and 65d in the bottom segment 61 of insert 60. When the second adapter 150 is in place in receptacle 40, its end wall 155 is toward the crown tooth 22, as shown in FIGS. 10 and 11.

The second adapter 150 has a flat top wall 157 extending from the upper end of its end wall 155 parallel to its bottom wall 151. The vertical thickness of top wall 157 is 1.0 mm. It has a rectangular opening 158 for snugly but slidably receiving the bottom segment 61 of insert 60. Top wall 157 projects from end wall 155 about 1.5 mm. farther than bottom wall 151.

When the second adapter 150 is in the receptacle 40, together they provide a second socket for snugly receiving the bottom segment 61 of insert 60. Because the bottom of the second adapter is shorter by about 0.5 mm. than the end-to-end dimension of the receptacle recess 47, this second socket is slidable end-to-end through a distance of 0.5 mm. in the receptacle.

The tooth positioning kit preferably includes a spacer 68 (FIG. 7) having a thickness of substantially 0.5 mm. between its opposite flat major faces.

An identical positioning kit is provided for the other neighbor tooth unit 24–24a.

As shown in FIG. 8, the crown that is to be fitted on the artificial tooth 22 has a thin metal inner liner or "coping" 70 covered by porcelain tooth material 71. The metal coping, which is about 0.2 mm. thick, is applied to artificial tooth 22 with a suitable epoxy resin adhesive. Then a wet mixture of porcelain powder and distilled water is "packed" on the coping. When baked in an oven, the wet porcelain will shrink about 0.5 mm. on each side and about 1.0 mm. on top. Since the wet porcelain crown is larger than the finished baked crown will be, the problem is: how to remove crown tooth unit 22–22a and the wet crown from between the neighbor teeth 23 and 24. In accordance with the present invention, this problem is solved by temporarily positioning the neighbor teeth farther from the crown tooth 22 than the positions of the corresponding natural teeth in the patient's mouth.

FIG. 10 shows the second adapter 150 received in the receptacle 40, with the end wall 155 of the adapter at the end of the receptacle recess 47 toward the crown tooth 22. The bottom wall 151 of this adapter engages the bottom wall 41 of receptacle 40, and the top wall 157 of the adapter overlies the top surface 40b of receptacle 40 and the adjacent base surface 20b at the bottom of gap 27. When the tooth-supporting insert 60 is received in the second adapter, the corresponding neighbor tooth unit 23–23a is 0.5 mm. farther from the crown tooth unit 22–22a than the natural tooth in the patient's mouth is. Also, the neighbor tooth 23 is 1.0 mm. farther from the base 21 than the position of the corresponding tooth in the patient's mouth. This is to compensate for the expected shrinkage of the wet porcelain crown when it is baked. The spacer 68 may be slidably inserted between the neighbor tooth segment 25–23a and the next tooth 25 and its gum segment 25a to hold the neighbor tooth unit 23–23a stabilized. (The original gap 27 between teeth 23 and 25 has been reduced from 1 mm. to 0.5 mm. because of the new position of neighbor tooth 23 0.5 mm. farther from crown tooth 22.)

The neighbor tooth 24 on the opposite side of crown tooth 22 is similarly mounted on second adapter 150 received in the receptacle 40 on that side and receiving the insert 60 to which gum segment 24a and tooth 24 are attached. Neighbor tooth 24 is about 0.5 mm. away from crown tooth 22 and it is 1.0 mm. farther out from the base 20 than the position of the corresponding tooth in the patient's mouth.

The dental technician adds wet porcelain to the crown 71 at this time, as shown in phantom in FIG. 10, while neighbor teeth 23 and 24 are in these retracted positions. This is called "packing". The technician packs the crown until the wet porcelain on top in FIG. 10 is at substantially the same level as the neighbor teeth 23 and 24.

Next, the spacer 68 may be removed, permitting the neighbor tooth unit 23–23a, insert 60 and adapter 150 to be slid as a unit 0.5 mm. farther away from crown tooth 22 and toward tooth 25 to the position shown in FIG. 11. This provides an additional clearance for the adjacent side of crown tooth 22 and its crown 70,71. The same positioning change is provided for the neighbor tooth 24 on the opposite side of crown tooth 22.

With both neighbor teeth 23 and 24 retracted as much as possible from tooth 22 and its crown, this tooth and its crown may be removed from the base and put in an oven where it is baked at 1800 degrees F. in vacuum, causing the porcelain to shrink about 0.5 mm. on each side of the crown and about 1.0 mm. on top.

Following this, the crowned artificial tooth 22 is reinserted on the base 20 of the dental model between the retracted neighbor teeth 23 and 24. Next, each of the neighbor tooth units 23–23a and 24–24a is removed from the base 20 along with the corresponding tooth support insert 60 and the corresponding second adapter 150. That adapter is removed and is replaced on the insert 60 by the first adapter 50 (FIG. 2) and this assembly is inserted in the base-mounted receptacle 40, as shown in FIG. 4. This puts each neighbor tooth 23 and 24 in exactly the position of the corresponding tooth in the patient's mouth. This enables the dental technician to determine whether the baked crown 70,71 on tooth 22 is exactly the right size.

If it is too small on a side toward either neighbor tooth 23 or 24, the neighbor teeth are repositioned as shown in FIG. 10 and the technician "packs" the crown with more porcelain. Then the neighbor teeth are retracted even farther (FIG. 11) and the crowned tooth is removed from base 20. First, it is heated at about 1200 degrees F. to dry the newly applied porcelain and then it is baked at 1800 degrees F. to fuse it to the underlying porcelain and form an integral monolith.

Then, after tooth 22 and its rebaked crown are reinserted on the base, the neighbor teeth 23 and 24 may be repositioned as shown in FIG. 12 for tooth 23 if additional porcelain must be added to the crown.

As shown in FIG. 4, an opening 123 extends through the base 20 of the dental model in alignment with the bottom opening 42 in the receptacle 40 below neighbor tooth 23. Similarly, an opening 124 extends through the base in alignment with the bottom opening in the receptacle below the other neighbor tooth 24. If the dental technician has any difficulty in removing the tooth-support insert 60 from either the first adapter 50 (FIG. 4) or the second adapter 150 (FIG. 11) in the positioning kit for either neighbor tooth 23 or 24, he or she may insert a slender push rod through the base opening 123 or 124 to engage the inner end of the corresponding tooth-support insert and push it out of the adapter.

While the invention has been described with reference to the manufacture of a single-tooth crown, it is to be understood that it may also be used in the manufacture of multiple-tooth crowns.

I claim:

1. In a dental model for use in manufacturing a dental crown for a patient, said model including:
   a rigid base;
   a rigid pedestal on said base substantially duplicating the patient's gum;
   and a plurality of artificial teeth attached to said pedestal on the opposite side of the pedestal from said base, said artificial teeth substantially duplicating the patient's teeth along said gum and including a first artificial tooth which is to be fitted with a dental crown, said pedestal including a first gum segment between said first artificial tooth and said base which is separate from the base and from the rest of the pedestal, said first tooth and said first gum segment constituting an integral crown tooth unit in the dental model;
   and pin-and-socket locating means on said base and said first gum segment to position said first artificial tooth at the precise location of the corresponding tooth in the person's mouth, said locating means permitting the slidable removal of said crown tooth unit substantially perpendicularly away from said base;
   the improvement wherein:
   said pedestal has a neighbor gum segment next to said first gum segment which is separate from the rest of the pedestal and from the base, said neighbor gum segment carrying an artificial neighbor tooth which is next to said first artificial tooth, said neighbor tooth and said neighbor gum segment constituting an integral neighbor tooth unit in the dental model;
   and said model presents a gap between said neighbor tooth unit and the next tooth and the corresponding gum segment of the pedestal;
   and further comprising:
   positioning means acting between said base and said neighbor gum segment of said neighbor tooth unit for selectively positioning said neighbor tooth unit on said base either (1) at a normal location in which said neighbor tooth is at the precise location of the corresponding tooth in the patient's mouth or (2) at a displaced location extending into said gap and positioning said neighbor tooth farther from said first tooth, thereby making room for the addition of wet porcelain to a crown on said first tooth and facilitating the slidable removal of said crown tooth unit from the base.

2. A dental model according to claim 1 wherein said positioning means comprises:
   a receptacle in said base defining a recess which is open toward said neighbor tooth unit;
   a first adapter shaped and dimensioned to be snugly seated in said receptacle recess and to be removable therefrom, said first adapter when seated in said receptacle recess providing with said receptacle a first socket which is open toward said neighbor tooth unit;
   an insert attached to said neighbor gum segment of said neighbor tooth unit and shaped and dimensioned to be snugly received in said first socket provided by said first adapter and said receptacle to position said neighbor tooth unit in said normal location;
   a second adapter shaped and dimensioned to be received in said receptacle recess to provide therewith a second socket which is open toward said neighbor tooth unit and which is shaped and dimensioned to snugly receive said insert;
   said insert when received in said second socket provided by said receptacle and said second adapter therein positioning said neighbor tooth unit in said displaced location.

3. A dental model according to claim 2 wherein:
   said second adapter is slidably adjustable in said receptacle recess toward said gap to position said neighbor tooth unit farther away from said first tooth than said displaced location.

4. A dental model according to claim 3 wherein:
   said first adapter is a generally channel-shaped body having a bottom wall engageable with the bottom of said receptacle recess and opposite end walls engageable with said receptacle recess at its opposite ends;
   and said second adapter has a bottom wall engageable with the bottom of said receptacle recess and an end wall joined to said bottom wall at one end thereof, said end wall of the second adapter having a thickness such that, when it engages the end of said receptacle recess toward said first tooth, said second adapter positions said neighbor tooth unit at said displaced location.

5. A dental model according to claim 4 wherein:
   said bottom wall of the second adapter is shorter than the end-to-end dimension of said receptacle recess, thereby enabling said second adapter to be positioned in said receptacle recess with its end wall spaced away from said end of the receptacle recess.

6. A dental model according to claim 5 wherein:
said bottom wall of the second adapter is substantially thicker than said bottom wall of the first adapter, whereby to position said neighbor tooth unit away from the base when said second adapter is received in said receptacle recess and said insert is received in said second socket.

7. A dental model according to claim 6 wherein:
said second adapter has a top wall extending from the upper end of its end wall parallel to its bottom wall, said top wall of the second adapter extending in the same direction as its bottom wall and farther than its bottom wall for overlying engagement with the base at the bottom of said gap.

8. A dental model according to claim 4 wherein:
said bottom wall of the second adapter is substantially thicker than said bottom wall of the first adapter, whereby to position said neighbor tooth unit away from the base when said second adapter is received in said receptacle recess and said insert is received in said second socket.

9. A dental model according to claim 8 wherein:
said second adapter has a top wall extending from the upper end of its end wall parallel to its bottom wall, said top wall of the second adapter extending in the same direction as its bottom wall and farther than its bottom wall for overlying engagement with the base at the bottom of said gap.

10. A dental model according to claim 4 wherein:
said second adapter has a top wall extending from the upper end of its end wall parallel to its bottom wall, said top wall of the second adapter extending in the same direction as its bottom wall and farther than its bottom wall for overlying engagement with the base at the bottom of said gap.

11. A dental model according to claim 10 wherein:
said bottom wall of the second adapter is shorter than the end-to-end dimension of said receptacle recess, thereby enabling said second adapter to be positioned in said receptacle recess with its end wall spaced away from the end of the receptacle recess which is toward said first tooth.

12. A dental model according to claim 2 wherein:
said first adapter is a generally channel-shaped body having a bottom wall engageable with the bottom of said receptacle recess and opposite end walls engageable with said receptacle recess at its opposite ends;
and said second adapter has a bottom wall engageable with the bottom of said receptacle recess and an end wall joined to said bottom wall at one end thereof, said end wall of the second adapter having a thickness such that, when it engages the end of said receptacle recess toward said first tooth, said second adapter positions said neighbor tooth unit at said displaced location.

13. A dental model according to claim 12 wherein:
said bottom wall of the second adapter is shorter than the end-to-end dimension of said receptacle recess, thereby enabling said second adapter to be positioned in said receptacle recess with its end wall spaced away from said end of the receptacle recess.

14. A dental model according to claim 12 wherein:
said bottom wall of the second adapter is substantially thicker than said bottom wall of the first adapter, whereby to position said neighbor tooth unit away from the base when said second adapter is received in said receptacle recess and said insert is received in said second socket.

15. A dental model according to claim 14 wherein:
said second adapter has a top wall extending from the upper end of its end wall parallel to its bottom wall, said top wall of the second adapter extending in the same direction as its bottom wall and farther than its bottom wall for overlying engagement with the base at the bottom of said gap.

16. A dental model according to claim 12 wherein:
said second adapter has a top wall extending from the upper end of its end wall parallel to its bottom wall, said top wall of the second adapter extending in the same direction as its bottom wall and farther than its bottom wall for overlying engagement with the base at the bottom of said gap.

17. A dental model according to claim 16 wherein:
said bottom wall of the second adapter is shorter than the end-to-end dimension of said receptacle recess, thereby enabling said second adapter to be positioned in said receptacle recess with its end wall spaced away from the end of the receptacle recess which is toward said first tooth.

* * * * *